(12) United States Patent
Scott

(10) Patent No.: US 7,217,249 B2
(45) Date of Patent: May 15, 2007

(54) ADJUSTABLE HINGE JOINT SUPPORT

(75) Inventor: John Scott, Dallas, TX (US)

(73) Assignee: New Options Sports, Dallas, TX (US)

( * ) Notice: Subject to any disclaimer, the term of this patent is extended or adjusted under 35 U.S.C. 154(b) by 473 days.

(21) Appl. No.: 10/376,975

(22) Filed: Feb. 27, 2003

(65) Prior Publication Data

US 2003/0176826 A1 Sep. 18, 2003

Related U.S. Application Data

(60) Provisional application No. 60/361,901, filed on Feb. 28, 2002.

(51) Int. Cl.
*A61F 5/00* (2006.01)

(52) U.S. Cl. .......................... 602/23; 602/26

(58) Field of Classification Search ............... 602/4–5, 602/16, 26; 128/882
See application file for complete search history.

(56) References Cited

U.S. PATENT DOCUMENTS

| | | | |
|---|---|---|---|
| 3,913,302 A * | 10/1975 | Centers .......................... 54/65 |
| 4,130,115 A * | 12/1978 | Taylor .......................... 602/16 |
| 4,287,885 A * | 9/1981 | Applegate .................... 602/26 |
| 4,494,534 A * | 1/1985 | Hutson ........................ 602/16 |
| 4,585,003 A | 4/1986 | Meistrell | |
| 4,628,916 A * | 12/1986 | Lerman et al. ............... 602/16 |
| 4,700,406 A | 10/1987 | Meistrell | |
| 4,706,673 A | 11/1987 | Meistrell | |
| 4,729,370 A | 3/1988 | Kallassy | |
| 4,805,606 A * | 2/1989 | McDavid, III ............... 602/26 |
| 4,805,620 A | 2/1989 | Meistrell | |
| 4,841,957 A | 6/1989 | Wooten et al. | |
| 4,856,501 A | 8/1989 | Castillo et al. ............... 128/80 |
| 4,873,967 A | 10/1989 | Sutherland ................... 128/80 |
| 4,986,264 A | 1/1991 | Miller .......................... 128/80 |
| 5,050,620 A | 9/1991 | Cooper | |
| 5,086,761 A * | 2/1992 | Ingram ........................ 602/26 |
| 5,261,871 A * | 11/1993 | Greenfield ................... 602/26 |
| 5,554,104 A | 9/1996 | Grim ............................. 602/8 |
| 5,562,605 A | 10/1996 | Taylor ......................... 602/26 |
| 5,624,389 A | 4/1997 | Zepf ............................ 602/26 |
| 5,658,243 A | 8/1997 | Miller et al. ................. 602/26 |
| 5,792,084 A * | 8/1998 | Wilson et al. ................ 602/13 |
| 5,795,312 A * | 8/1998 | Dye ............................ 601/151 |
| 5,810,752 A | 9/1998 | Grifka ......................... 602/16 |
| 5,857,988 A | 1/1999 | Shirley ........................ 602/26 |
| 5,921,946 A | 7/1999 | Tillinghast et al. .......... 602/16 |
| 6,066,110 A | 5/2000 | Nauert ........................ 602/26 |
| 6,120,472 A | 9/2000 | Singer, Jr. | |

* cited by examiner

*Primary Examiner*—Michael A. Brown
(74) *Attorney, Agent, or Firm*—Winstead PC

(57) ABSTRACT

A brace for supporting the knee of the wearer. The brace has an adjustable support mechanism for accommodating a variety of leg shapes. The hinge portion of the brace is adjustable so that there is proper balanced support on opposite sides of the knee. Furthermore, the brace is universal in applicability and may be used on either the right or left leg.

16 Claims, 6 Drawing Sheets

ADJUSTABLE HINGE JOINT SUPPORT

CROSS-REFERENCE

This application claims priority from and incorporates the entire disclosure of U.S. Provisional Patent Application No. 60/361,901 filed Feb. 28, 2002.

BACKGROUND

1. Technical Field of the Invention

The present invention relates to orthopedic supports and, more particularly, but not by way of limitation, to an orthopedic support for a knee having a hinge that may be adjustably positioned for anatomically correct support of knees and legs of varying sizes and shapes.

2. History of Related Art

It is common in the Sports Medicine Industry to utilize orthopedic supports for various body parts subject to injury. The most common support areas include the knees, elbows, and ankles. Often injuries to these areas of the body can be treated by the utilization of the appropriate orthopedic support. In the event surgery, rehabilitation is sometimes augmented by the utilization of such supports.

The design of orthopedic supports has changed considerably over the past two decades. The types of material used as well as the fastening and hinging mechanisms associated with orthopedic supports have been the subject of considerable study and improvement. U.S. Pat. No. 4,986,264 to Miller, teaches a knee brace having an interior tibial shell and an interior femoral which are closely configured to the shape of the lower leg and thigh respectively and which are joined by a frame in the form of a pair of polycentric hinge joints. U.S. Pat. No. 4,856,501 to Castill et. al. teaches a knee brace having adjustable width frame pivoted to cuffs. The brace as set forth therein includes first and second frame members disposed on opposite sides of the joint to be supported, and first and second hinge members disposed substantially adjacent to joint and connected to the frame members to pivot the frame members about the joint.

Another example of related art is shown in U.S. Pat. No. 4,494,534 to Hudson. This patent teaches a universal leg brace system for controlling the degree of motion permitted by wearer's knee characterized by respective flexible sheets of cushioned material adapted for snugly wrapping around the wearer's thigh and calf. U.S. Pat. No. 5,554,104 to Grim likewise teaches a custom formed knee brace. This brace is taught to support weakened or injured knees by having formed components which conform to the unique configuration of an individual's leg surfaces. Other references include U.S. Pat. No. 6,066,110 to Nauert; U.S. Pat. No. 5,810,752 to Grifka; U.S. Pat. No. 5,624,389 to Zepf; U.S. Pat. No. 4,873,967 to Sutherland; U.S. Pat. No. 5,921,946 to Tillinghas; and U.S. Pat. No. 5,562,605 to Taylor.

As seen from the patents listed above, the aspect of joint support, flexibility, and rehabilitation have received considerable attention in prior orthopedic support design. One area of continued concern is, however, the adaptability of a single support to human body parts of varying size and shape. For example, knee braces require that the area of the thigh above the knee as well as the area of the leg beneath the knee be securely fitted within the brace. Some legs are shaped differently than others. Some individuals have larger thighs than other individuals and thus various modifications must be made to the particular brace to accommodate large and/or smaller leg portions. This is particularly true when an upper leg portion in the area of the thigh is considerably larger than the portion below the knee. When hinge structures are utilized in conjunction with orthopedic supports for such knees, the appropriate alignment of the oppositely disposed hinges becomes critical. If the hinges are not diametrically opposed one to the other, the appropriate hinge action cannot smoothly occur. In fact, various stresses can be imparted to the orthopedic support as well as the knee when misalignment is present. Such a problem is contrary to the purpose of the orthopedic support and will not maximize efficiency and healing. The alignment of the hinges should, therefore, be a primary consideration in orthopedic support design construction and fitting. The present invention addresses such design manufacturer and fitting issues by providing an orthopedic support with adjustable hinge sections to permit appropriate diametrically opposed hinge alignment therewith to accommodate a variety of a body shapes and sizes.

SUMMARY OF THE INVENTION

The present invention relates generally to orthopedic supports having hinge elements associated therewith. More particularly, one aspect of the invention includes an orthopedic support facilitating better fit for legs of varying shape, including the cone-shaped leg and the positioning of the support around the thigh. In one aspect of the present invention, hinges disposed for positioning above the patella have unique hook and pile adjustments to fit larger or smaller thighs (from child sizes to adult sizes) and allow proper balanced support on opposite sides of the knee. In another aspect a posterior elastic segment on velcro straps prevent any tourniquet effect. Moreover, the present invention may, in one embodiment, provide a universal right or left leg applicability with removable, adjustable half-horseshoe buttress.

Another aspect of the present invention relates to a hinged knee support utilizing adjustable hinges. The knee support is particularly adapted for individuals having larger thigh regions. Thus, the hinged knee support is adapted to open in the upper region thereof to accommodate various sizes and shapes of thigh portions and to further include means for adjustably positioning the lateral hinges so that they are oppositely disposed about knee to provide the most appropriate support, irrespective of the shape and size and In another aspect of the present invention, the present invention includes a large popliteal opening for added comfort by the user. A multitude of hinges may be used including both the single axis and a polycentric type of hinge.

In still another aspect of the present invention, a spiral stay may be used so that as the knee is bent by a user, the stay encourages the present invention to return to a neutral position after each movement. In this manner, as the knee is returned to a neutral position such that pressure exerted on the knee neither pushes or pulls the tissues of the knee apart.

In yet another aspect of the present invention, hook and pile inter-engagement is used to facilitate the positioning and securement of the hinges in the most appropriate location relative to the knee.

And yet a further aspect of the present invention, a hinged knee support is provided with a patient friendly configuration having a closed bottom section for covering the calf of the patient and an upper region that may be open and adjusted to the appropriate size for accommodating a variation in the size of the thigh of the user. The hinged knee further incorporates the adjustable hinge feature as described above therein facilitating structural support of patients having a wide variation of certain anatomical regions thereof.

BRIEF DESCRIPTION OF THE DRAWINGS

A more complete understanding of embodiments of the present invention can be achieved by reference to the following Detailed Description when taken in conjunction with the accompanying Drawings wherein:

FIG. 2 is an enlarged, side elevation, fragmentary view of the hinged attachment area of the knee support of FIG. 1 illustrating various positioning of the hinge thereon and a means of for attachment thereto;

DETAILED DESCRIPTION

It has been discovered that many commercial braces do not fit certain sizes and shapes in the most appropriate manner. This is particularly true of legs with large thighs and smaller calf regions. These leg shapes are referred to herein as "cone-shaped" legs and illustrated in certain ones of the following drawings. Further, the present invention may be adapted to fit the leg shapes of both children and adults.

Figure 1:
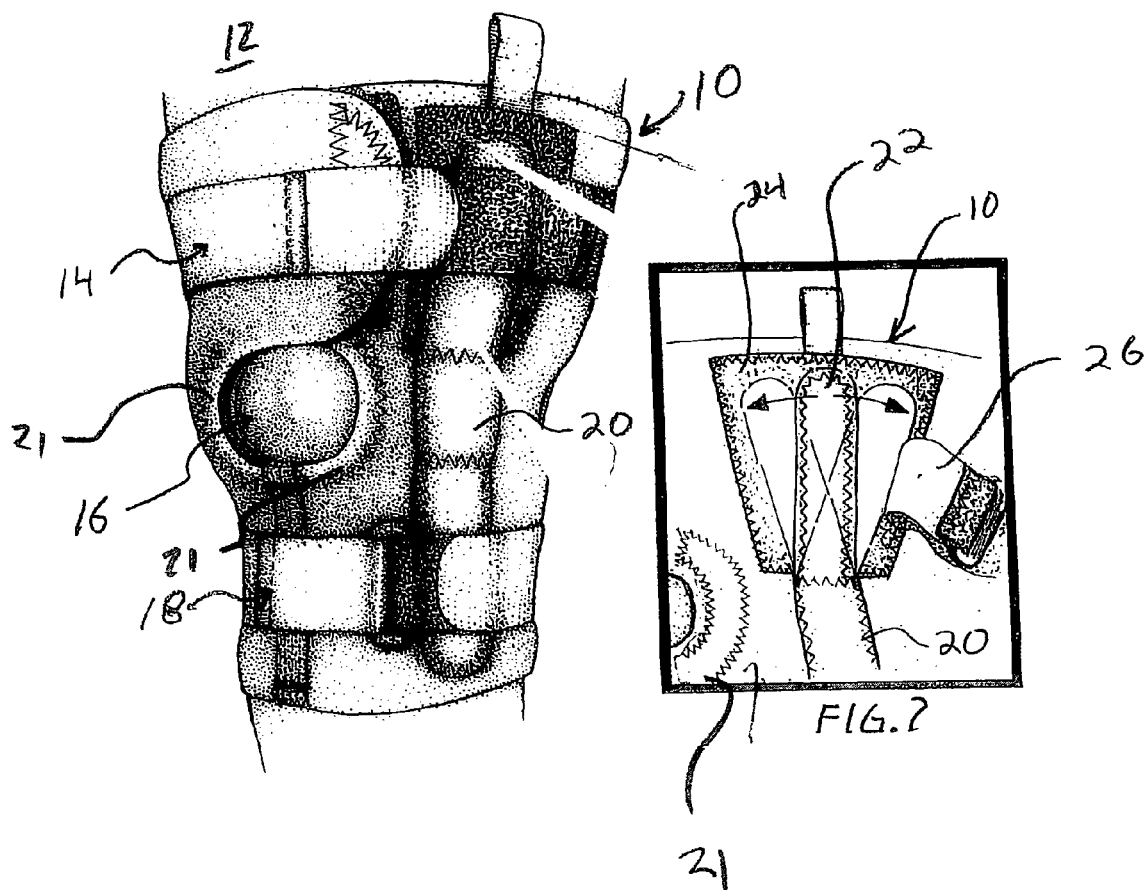
FIG. 1 is a perspective view of an orthopedic support constructed in accordance with the principles of the present invention.

Referring now to FIG. 1, there is shown an adjustable hinged knee support 10 constructed in accordance with the principles of the present invention. The knee support 10 facilitates a better fit for users having large thighs or "cone-shaped" legs 12. An adjustable upper fastener assembly 14 accommodates the various thigh sizes. As shown in FIG. 1, a large patella opening 16 (or alternatively, a large popliteal opening) is also provided for added comfort. On opposite sides of opening 16 are removable, adjustable half-horseshoe buttress' 21 for comfort and support (see also FIG. 2). As described below, the upper fastener assembly 14 and the lower fastener assembly 18 may be constructed with hook and pile portions to facilitate adjustability and ease of use by the user. Still referring to FIG. 1, a hinge 20 is distinctly placed along the medial portion of the knee support 10. Hinge 20 may be either a polycentric (double axis) hinge, single axis hinge, complex hinge, or a spiral stay. Other types of hinges may also be used As will be shown in more detail below, a second hinge 20 is disposed opposite hinge 20, and is positioned on the outside portion of the knee to balance the support about the knee. It has been observed in prior art that knee braces do not accommodate variations in size of the user's thigh, the position of the respective hinges may vary in accordance with the principles of the present invention.

Referring now to FIG. 2 there is shown an enlarged fragmentary, side elevation view of an upper portion 22 of hinge 20 of the knee support 10 of FIG. 1. The position of the upper portion 22 of hinge 20 is shown to be positionable about a hook and pile surface 24 of the knee support 10. A retaining strap 26 is shown in a position for securement of hinge 20. In this manner, the position of the hinge 20 relative to the leg of the user, as shown in FIG. 1, may be selectively adjusted to accommodate variations in the size of the thigh of the user. In other words, the medial and lateral hinges (described below) are adjusted to allow the knee support 10 to be anatomically correct relative to the knee.

Figure 3:
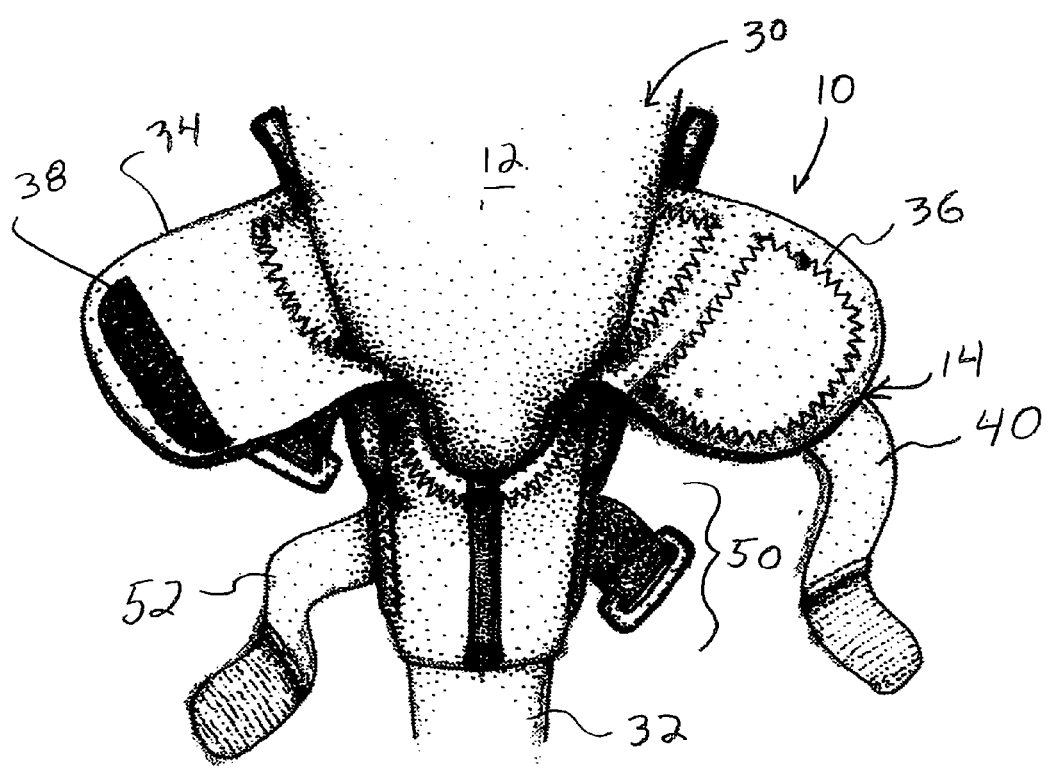
FIG. 3 is a front elevation view of the knee support of FIG. 1 illustrating the accommodation of a relatively large thigh therein and the manner of accommodation provided in accordance with the principles of the present invention.

Referring now to FIG. 3 there is shown the knee support 10 positioned about the leg 12 of a user. In this particular embodiment it may be seen that the thigh 30 is much larger than the calf 32 of the user. For this reason, the knee support 10 is constructed with opposing flaps 34 and 36 which as shown in FIG. 1, when closed comprise an upper portion 52 of the knee support 10. In this particular illustration, it may be seen that the flaps 34 and 36 are in an open position, which permit the fitting of the knee support 10 about the leg 12 of the user. The flaps 34 and 36 are constructed with hook and pile surfaces 38 (one which is shown on flap 34) to facilitate securement about the leg 12 of the user. A portion of the hook and pile surface 38 comprises a portion of the adjustable upper fastener assembly 14, illustrated in FIG. 1. The adjustable upper fastener assembly 14 further includes a strap 40 extending outwardly from flap 36. Still referring to FIG. 3, the lower region 50 of the knee support 10, in this particular embodiment, is of fixed size and thus is not adjustable. The lower region 50 does, however, include a support strap 52 that affords securement of the knee support 10 about the leg 12 of the user.

Figure 4:
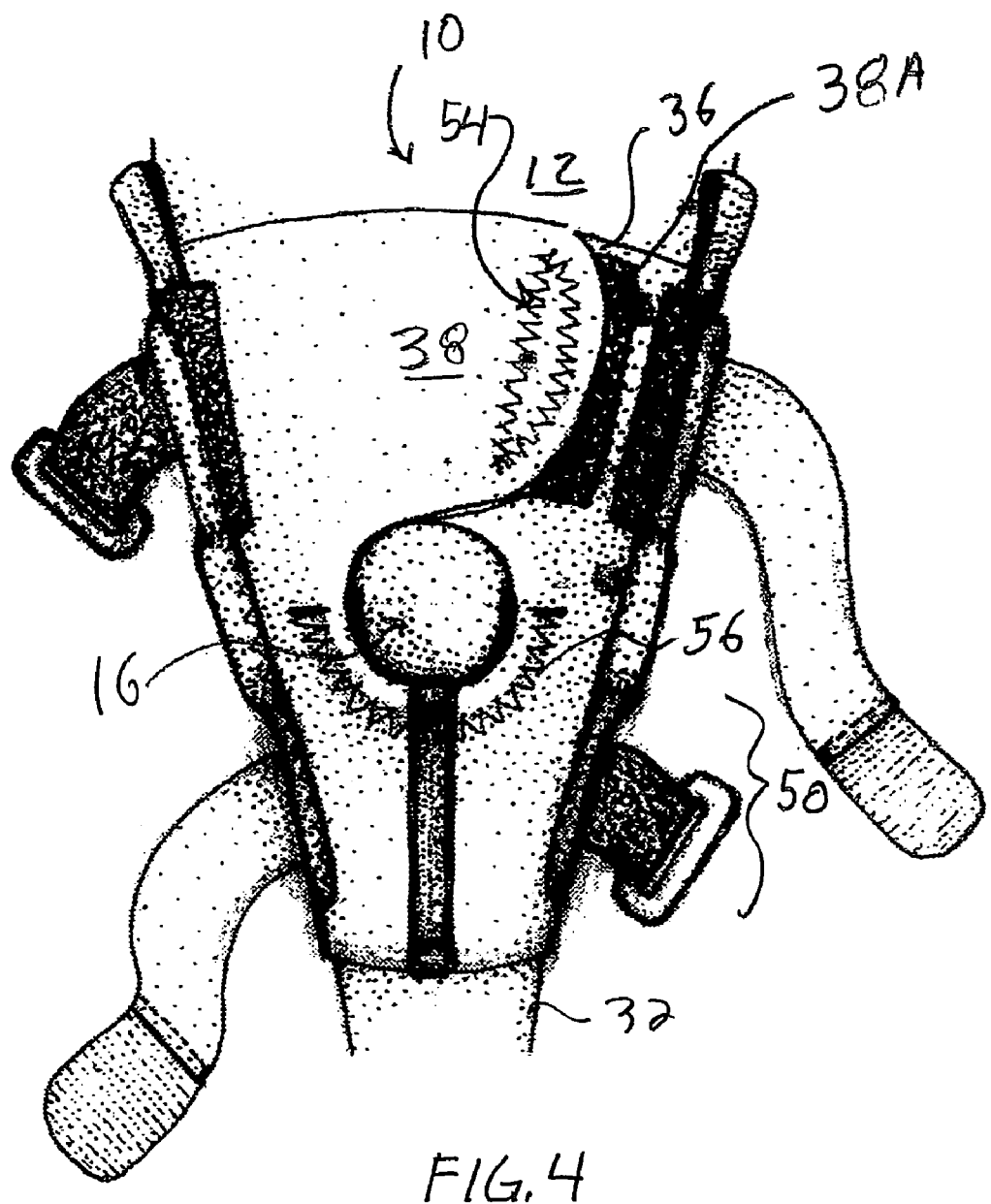
FIG. 4 is a front elevation view of the knee support of FIG. 3 illustrating closure of the kneec thigh and the use of hook and pile closure straps for securement of the knee support to the user's leg.

Referring now to FIG. 4 there is shown the knee support 10 of FIG. 3 positioned about the leg 12 of the user with the flap 38 closed and positioned over the flap 36 as described above. A region 38a of hook and pile material, which is not visible in FIG. 3, is illustrated as it appears on the outer portion of the flap 36. It should be noted that the term "hook and pile fasteners" is a recognized structure to one skilled in the art and is often sold under the trademark Velcro®. It is also well known that the hook and pile enter and engage one another. Therefore, if surface 38, as shown in FIG. 3, is a hook surface then the region 38a of FIG. 4 would be a pile surface. It is to be understood that further reference herein to a "hook and pile surface" refers to either a hook or a pile surface.

Still referring to FIG. 4, it may be seen that the lower region 50 of the knee support 10 conforms about the calf 32, with the patella opening 16 more clearly illustrated by the closure of flap 38 over flap 36. Various stitching 54 is shown upon flap 38 as well as stitching 56 shown around the patella opening 16. This stitching is shown for purposes of illustration only, and other stitching embodiments maybe incorporated herein. All illustrations thereof should not be deemed limited in any respect relative to the principles of the present invention.

Figure 5:
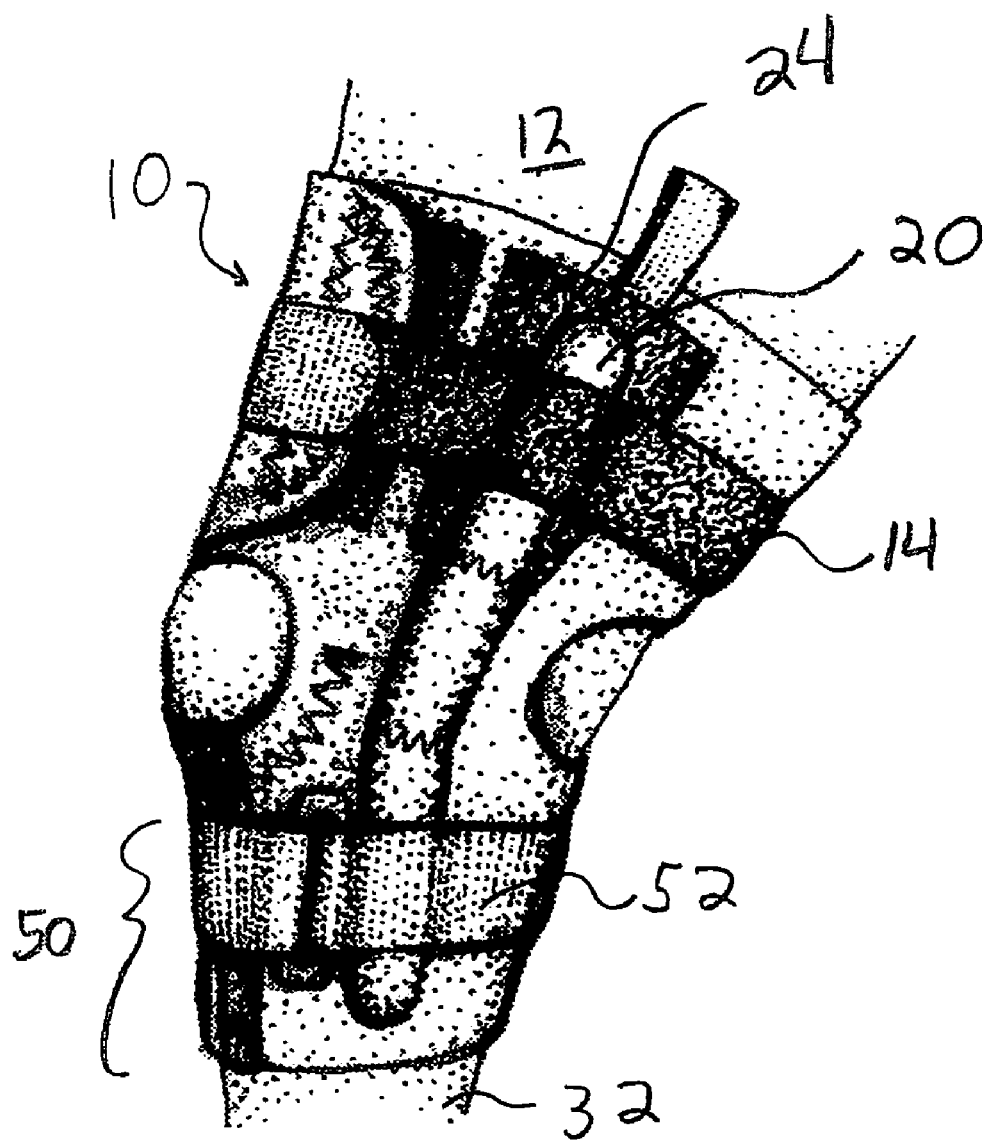
FIG. 5 is a side elevation view of the knee support of FIG. 1 further illustrating the construction of thereof.

Referring now to FIG. 5 there is shown the knee support 10 with the lower strap 52 securing the lower region 50 of the knee support 10 while the upper fastener assembly 14 secures the upper region of the knee support knee 10 about the leg 12 of the user. It may be seen that the hinge 20 is positioned on the hook and pile surface 24 in a position most appropriate to support of knee of the user as will be described in more detail below.

Figure 6:
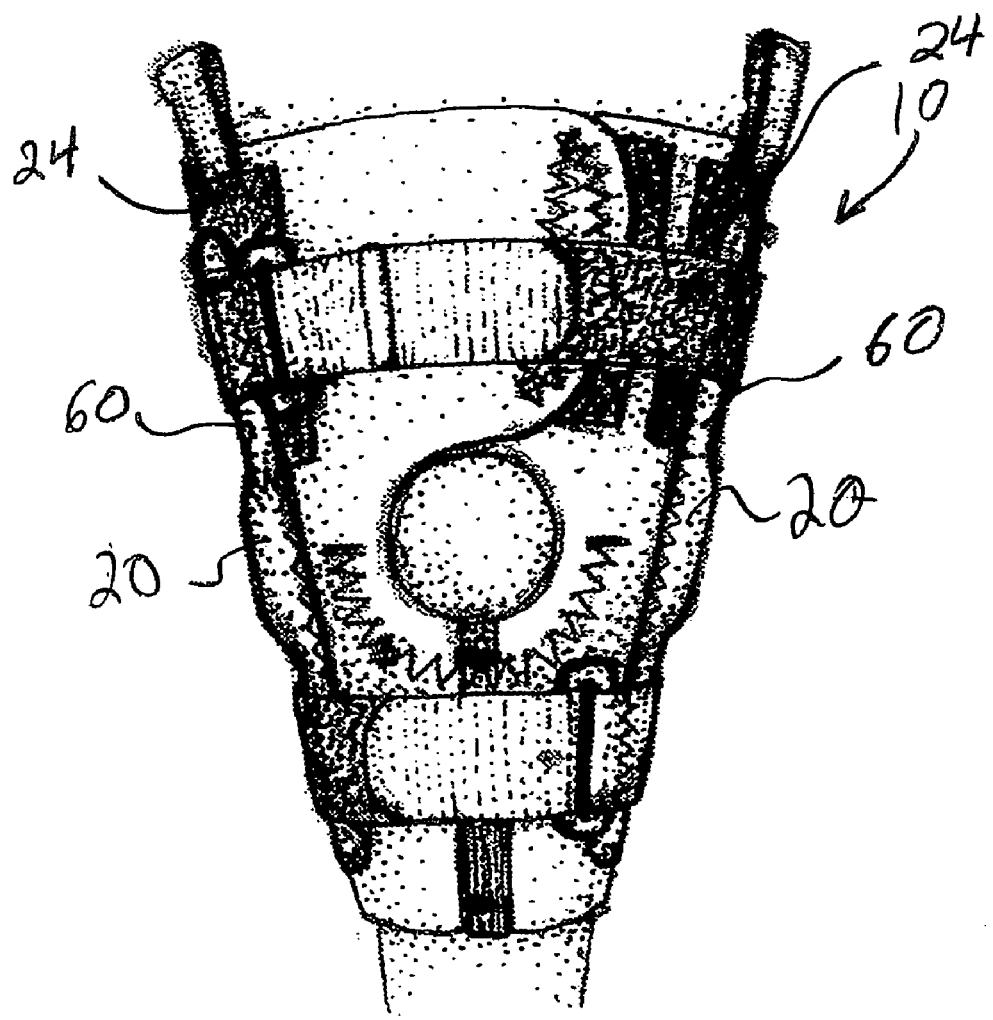
FIG. 6 is a front elevation view of the knee support of FIG. 1 further illustrating the construction thereof and the positioning of the medial and lateral hinges so that said hinges are anatomically correct relative to the knee of the user.

Referring now to FIG. 6, there is shown the knee support 10 in a front elevation view. This particular view it may be seen that the hinge 20 comprises medial and lateral hinges 20. Because the knee brace may be used on either left or right knees, it is not necessary to differentiate which hinge 20 is medial or lateral. This definition is relative to the leg of the user. The present description is intended to provide an understanding that the position of the medial and lateral hinges 20 may be adjusted so that they are anatomically correct. As described above, the ability to adjust the position of the hinges 20, and the ability to position the upper portion 22 of the hinge 20 about the hook and pile surface 24 against which it may be secured, facilitates anatomically correct adjustment.

In one embodiment of the present invention, a sheet of material 60 covers the hinge 20. The underside of the sheet 60 has a mating hook and pile surface to engage the hook and pile surface 24, which provides securement of the upper portion 22 of hinge 20 (FIG. 2) thereto.

In operation, the present invention accommodates various leg sizes. This is clearly shown in FIG. 3, where the above described upper fastener assembly 14 and strap 40 therein described allow the user to position the knee support 10 around the leg 12 of the user in a manner facilitating a wide variety of thigh sizes. Because thigh sizes will vary (especially between children and adults), the knee support 10 of the present invention may be provided in a variety of basic sizes, such as small, medium, large, and extra large, to further provide accommodation of varying leg sizes.

Still referring to FIGS. 1–6 in combination, FIG. 4 illustrates the anterior hook and pile closure "wrap around" configuration that affords ease in the use of the present invention. However, other fasteners can be used. Likewise FIG. 5 illustrates the securement of the bottom strap 52 of the present invention around the calf 32 of the user prior to the securement of the upper fastener assembly 14. This is the preferred method of securing the knee support 10 around the leg 12 of the user.

Finally, FIG. 6 clearly illustrates the ability to adjust the medial and lateral hinges 20 in an anatomically correct configuration relative to the legs of the user. It is necessary to provide the hinges 20 on opposite sides of the user's knee, no matter the shape of the user's thigh so as to provide appropriate support about the knee. Thus, the present invention, which utilizes hook and pile adjustable "wrap around" fasteners, provides a better fit for "cone-shaped" legs than those found in the prior art. The large patella opening 16 provides additional comfort, while a posterior elastic segment on the hook and pile straps 40 and 52 (FIG. 3) prevent any tourniquet effect. As described above, the adjustable, hinged knee support 10 with adjustable hinges is interchangeable for use on either the right or left leg.

Figure 7:
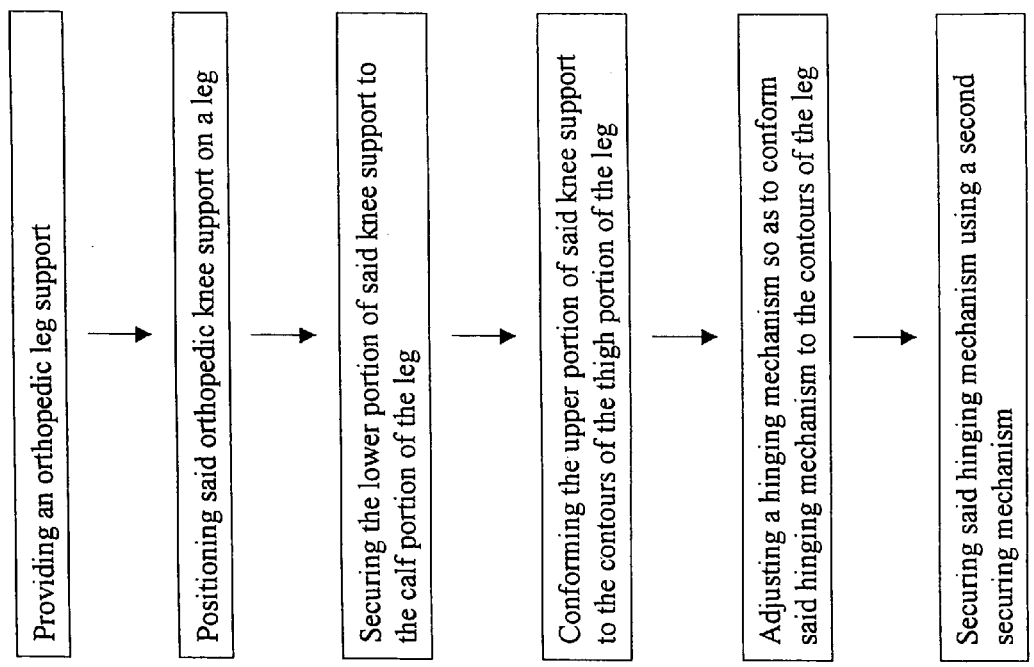
FIG. 7 is a flow chart illustrating the method of using the present invention.

Referring now to FIG. 7, the method of using the present invention allows users having different leg sizes and shapes, including a generally cone-shaped upper leg portion to be fitted with an effective knee support. The user positions the open knee support on the user's leg and adjusts the hinges as described above so as to position each hinge relative to the user's knees on opposite size thereof. The hook and pile fasteners permit the user to secure the hinge in the position that is most appropriate for the user's particular leg shape, and further secure the hinge with the straps pulled there around. It is possible to use multiple hinges, and in one aspect of the present invention four different hinges and/or stays may be used. It has been shown to the applicant that not everyone requires a heavy hinge and hinges that simply lockout at either 90 degrees or vertical are in some instances appropriate to prevent hyper extension of the user's knee. In accordance with the principles of the present invention, the use of a polycentric hinge (a double axis type of hinge) has also been found to be useful. It should be understood, however, that any type of hinge may be used.

One advantage of the present invention is the adjustable hinges. This is because adjustable hinges 20, as is illustrated in FIG. 2, allow the user to position the hinges 20 about the hook and pile material so as to position them above the knee wherein the hinges are neither to far interior nor to far posterior prior to final securement.

Another advantage is in the use of a flexible spiral stay, which allows use of the knee support 10 for various injuries where it is beneficial for the knee support apparatus to return to a neutral position for proper healing. Spiral stays are made from hardened, galvanized spring steel round wire which is coiled and flattened, and is generally referred to in the trade as "spiral boning". Such material provides support rigidity for partially immobilizing the knee, yet can be flexed, when placed under pressure, to conform to the body contours of the wearer, as illustrated in FIG. 5.

Yet another advantage is in the ample strap length provided, which allows a wide range of adjustability relative to the sizes of the user's leg. Since adjustability is a key aspect of the present invention, straps with hook and pile material are an advantage.

Finally, the present invention may be adapted to fit both children and adults. The present invention will be supplied in wide variety of sizes to accommodate the needs of various users.

Although an embodiment of the method and apparatus of the present invention has been illustrated in the accompanying Drawings and described in the foregoing Detailed Description, it will be understood that the invention is not limited to the embodiment disclosed, but is capable of numerous rearrangements, modifications and substitutions without departing from the spirit of the invention as set forth and defined herein.

What is claimed is:

1. A unitary adjustable hinged knee support apparatus adapted to accommodate a variety of leg shapes in association therewith, comprising:

an adjustable open upper-support portion adapted to receive an upper leg portion, and secured to said upper leg portion;

wherein said adjustable open upper-support portion comprises a first and a second flap operable to secure said adjustable upper-support portion to said upper leg, wherein said first flap comprises a hook and pile surface and said second flap comprises a mating hook and pile surface for mated engagement of said first flap to said second flap;

wherein said first and second flaps enable said adjustable open upper-support portion to be opened and adjusted to an appropriate size for accommodating a variation in an upper leg size of a user;

a non-adjustable closed lower-support portion adapted to receive a lower leg and secured to said lower leg;

wherein said non-adjustable closed lower-support portion is adapted to cover a calf of the user;

a plurality of flexible hinges adapted to be oppositely disposed about a patella;

wherein each of said plurality of flexible hinges comprises an upper, flexible portion;

wherein a position of the upper, flexible portion of said plurality of hinges is adjustable;

wherein said support apparatus further comprises an aperture aligned with the patella so as to facilitate comfortable wear by a user of said support apparatus;

wherein said support apparatus further comprises an aperture aligned with the popliteal portion of the knee so as to facilitate comfortable wear by a user of said support apparatus;

wherein said upper, flexible portion is operable to position said support apparatus in an anatomically correct manner relative to said knee; and wherein said upper, flexible portion of said plurality of hinges further comprise a hook and pile material operable to matingly engage said upper, flexible portion to said upper-portion in order to adjust said position of said upper, flexible portion.

2. The support apparatus of claim 1, wherein said plurality of hinges comprise at least two single axis hinges.

3. The support apparatus of claim 1, wherein said plurality of hinges comprise at least two polycentric hinges.

4. The support apparatus of claim 1, wherein said plurality of hinges comprise spiral stays.

5. The support apparatus of claim 1, further comprising a plurality of removable, adjustable half-horseshoe buttress' oppositely disposed about the aperture.

6. The support apparatus of claim 5, wherein said apparatus is sized to accommodate the needs of a child or an adult.

7. A unitary adjustable hinged knee support apparatus adapted to accommodate a variety of leg shapes in association therewith, comprising:

an adjustable open upper-support portion adapted to receive a thigh region of a user;

wherein said adjustable open upper-support portion comprises a first and a second flap operable to secure said adjustable upper-support portion to said thigh region, wherein said first flap comprises a hook and pile surface and said second flap comprises a mating hook and pile surface for mated engagement of said first flap to said second flap;

wherein said first and second flaps enable said adjustable open upper-support portion to be opened and adjusted to an appropriate size for accommodating a variation in a thigh size of the user;

a non-adjustable closed lower-support portion adapted to receive a calf region of the user;

a first hinge secured to said adjustable open upper-support portion and said non-adjustable closed lower-support portion;

at least a second hinge adapted to be oppositely disposed relative to said first hinge and secured to said adjustable open upper-support portion and said non-adjustable closed lower-support portion;

an upper, flexible portion of said first and at least a second hinge operable to secure said first and said at least second hinge about the knee in an anatomically correct position;

wherein a position of the upper, flexible portion of said first and said at least second hinge is adjustable;

wherein said upper, flexible portion of said first and said at least second hinge further comprises a hook and pile material operable to matingly engage said upper, flexible portion to said upper-support portion in order to adjust said position of said upper, flexible portion; and wherein a lower portion of said first and at least a second hinge is permanently secured to said non-adjustable closed lower-support portion of said unitary adjustable hinged knee support apparatus.

8. The support apparatus of claim 7, wherein said first hinge is aligned with the medial portion of said leg, and said at least a second hinge is aligned with the lateral portion of said leg.

9. The support apparatus of claim 8, wherein said support apparatus further comprises an aperture aligned with the patella so as to facilitate comfortable wear by a user of said support apparatus.

10. The support apparatus of claim 9, wherein said support apparatus further comprises an aperture aligned with the popliteal portion of the knee so as to facilitate comfortable wear by a user of said support apparatus.

11. The support apparatus of claim 10, wherein said first and at least a second hinge comprise single axis hinges.

12. The support apparatus of claim 10, wherein said first and at least a second hinge comprise polycentric hinges.

13. The support apparatus of claim 10, wherein said first and at least a second hinge comprise spiral stays.

14. A method of using an orthopedic unitary adjustable hinged knee support apparatus, comprising the steps of:

providing said orthopedic unitary adjustable hinged knee support apparatus;

positioning said support apparatus on a leg;

securing a non-adjustable closed lower portion of said support apparatus to a calf portion of the leg;

conforming an adjustable open upper portion of said support apparatus to the contours of a thigh portion of the leg;

wherein said adjustable open upper portion of said support comprises a first and a second flan operable to secure said adjustable upper portion of said support to said thigh portion of said leg, wherein said first flap comprises a hook and pile surface and said second flap comprises a mating hook and pile surface for mated engagement of said first flap to said second flap;

wherein said first and second flaps enable said adjustable open upper portion of said apparatus to be opened and adjusted to an appropriate size for accommodating a variation in a thigh size of a user;

adjusting a hinging mechanism so as to conform said hinging mechanism to the contours of the leg;

securing said hinging mechanism;

wherein said hinging mechanism comprises a plurality of flexible hinges adapted to be oppositely disposed about a patella;

wherein each of said plurality of flexible hinges comprises an upper, flexible portion;

wherein a position of the upper, flexible portion of said plurality of hinges is adjustable; and wherein said upper, flexible portion of said hinging mechanism further comprises a hook and pile material operable to matingly engage said upper, flexible portion to said upper-portion of said knee support in order to adjust said position of said upper, flexible portion.

15. The method according to claim 14, further comprising, prior to the step of positioning said support apparatus, the step of opening the upper portion of said knee apparatus.

16. The method according to claim 15, wherein the step of adjusting a hinging mechanism further comprises the steps of:

aligning the medial portion of the hinging mechanism so as to conform to the contours of the leg; and aligning the lateral portion of the hinging mechanism so as to balance support about the knee.

* * * * *

UNITED STATES PATENT AND TRADEMARK OFFICE
CERTIFICATE OF CORRECTION

PATENT NO. : 7,217,249 B2 Page 1 of 1
APPLICATION NO. : 10/376975
DATED : May 15, 2007
INVENTOR(S) : John Scott It is certified that error appears in the above-identified patent and that said Letters Patent is hereby corrected as shown below:

Column 8, line 30, claim 14      Replace "flan"
                                  With --flap--

Signed and Sealed this

Twenty-ninth Day of April, 2008

JON W. DUDAS
*Director of the United States Patent and Trademark Office*